(12) United States Patent
Kuiken et al.

(10) Patent No.: US 10,279,157 B2
(45) Date of Patent: May 7, 2019

(54) STRESS SHIELD AND INFECTION CONTROL FOR A SKIN-IMPLANT INTERFACE

(71) Applicant: Rehabilitation Institute of Chicago, Chicago, IL (US)

(72) Inventors: Todd A. Kuiken, Oak Park, IL (US); Gregory A. Dumanian, Chicago, IL (US); Jason M. Souza, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 123 days.

(21) Appl. No.: 14/213,318

(22) Filed: Mar. 14, 2014

(65) Prior Publication Data

US 2014/0276454 A1 Sep. 18, 2014

Related U.S. Application Data

(60) Provisional application No. 61/782,329, filed on Mar. 14, 2013.

(51) Int. Cl.
*A61M 39/10* (2006.01)
*A61M 1/00* (2006.01)
*A61M 39/02* (2006.01)

(52) U.S. Cl.
CPC .......... *A61M 39/10* (2013.01); *A61M 1/0023* (2013.01); *A61M 1/0088* (2013.01); *A61M 39/0247* (2013.01); *A61M 1/0056* (2013.01); *A61M 2039/0261* (2013.01); *A61M 2210/02* (2013.01)

(58) Field of Classification Search
CPC ................ A61M 1/0088; A61M 39/10; A61M 39/0247; A61M 1/0023; A61M 2210/02; A61M 1/0056; A61M 2039/0261; A61J 15/0053; A61F 2/7818; A61F 2/7812; A61F 2002/802; A61F 2002/7887; A61F 13/0203; A61F 13/0216; A61F 2013/00536; A61F 13/00068
USPC ......................................... 604/246, 319, 263
See application file for complete search history.

(56) References Cited

U.S. PATENT DOCUMENTS 4,959,054 A * 9/1990 Heimke ............ A61M 39/0247
604/175
5,636,643 A 6/1997 Argenta et al.
(Continued)

OTHER PUBLICATIONS

NPL STIC Search Jun. 20, 2017.*

*Primary Examiner* — Bhimsa Mehta
*Assistant Examiner* — Hamza A Darb
(74) *Attorney, Agent, or Firm* — Polsinelli PC; Ari M. Bai (57) ABSTRACT

Embodiments for superficial tissue compliance modulation and negative pressure wound therapy for stabilization of a chronic percutaneous implant are disclosed. An external cap is coupled to a compliance gradient of progressively decreasing stiffness. Together the external cap and compliance gradient act as a stress shield that allows forces that would otherwise act on the skin at the skin-implant interface to be dissipated over a larger area. In addition, negative pressure and fluids may be applied through negative pressure and fluid adapters, respectively, to the skin-implant interface, the status of which may be further monitored through the use of one or more sensors.

36 Claims, 5 Drawing Sheets

(56) References Cited

U.S. PATENT DOCUMENTS

| | | | | |
|---|---|---|---|---|
| 5,897,531 A * | 4/1999 | Amirana | ............... | A61M 25/02 |
| | | | | 128/DIG. 26 |
| 7,105,122 B2 * | 9/2006 | Karason | ................ | A61F 2/5046 |
| | | | | 264/314 |
| 2005/0004534 A1 * | 1/2005 | Lockwood | .......... | A61M 1/0031 |
| | | | | 604/304 |
| 2005/0222527 A1 * | 10/2005 | Miller | ................. | A61M 1/0088 |
| | | | | 602/1 |
| 2005/0261642 A1 * | 11/2005 | Weston | ............... | A61M 1/0031 |
| | | | | 604/313 |
| 2007/0060891 A1 * | 3/2007 | Skiera | ................... | A61F 2/2814 |
| | | | | 604/175 |
| 2007/0118096 A1 * | 5/2007 | Smith | .................... | A61B 5/445 |
| | | | | 604/541 |
| 2008/0051828 A1 | 2/2008 | Sample et al. | | |
| 2012/0157750 A1 * | 6/2012 | Robinson | .......... | A61F 13/00063 |
| | | | | 600/12 |
| 2012/0185060 A1 * | 7/2012 | Asgeirsson | ........... | A61F 2/7812 |
| | | | | 623/36 |

\* cited by examiner

STRESS SHIELD AND INFECTION CONTROL FOR A SKIN-IMPLANT INTERFACE

CROSS REFERENCE TO RELATED APPLICATIONS

This is a non-provisional application that claims benefit to U.S. provisional patent application Ser. No. 61/782,329 filed on Mar. 14, 2013 and is herein incorporated by reference in its entirety.

STATEMENT REGARDING FEDERALLY SPONSORED RESEARCH

This invention was made in part under USAMRAA contract #W81XWH-11-1-0720 and with philanthropic support from the George Link Jr. Foundation, Inc. The government has certain rights in this invention.

FIELD

The embodiments of the invention disclosed herein relate to a medical system for the treatment of percutaneous-implant sites, and more particularly to a superficial tissue compliance modulation and negative pressure wound therapy system for maintaining and treating chronic percutaneous implants.

BACKGROUND

Many diseases, impairments, and injuries are presently treated by medical devices that must be able to pass through the skin in order to treat a patient. A variety of medical devices exist that must pass through the skin to allow transfer of fluids, gases, skeletal loading, power, or other ingests between the external environment and the internal environment of the body. In addition, many of these through-skin or "percutaneous" devices must also remain in place for long time periods, or indefinitely.

For instance, indwelling catheters are used to provide access to various body compartments. Central venous catheters (also known as central lines) are used in intensive care medicine to provide ingests such as drugs, fluids, nutrition, or blood products over a long time periods—usually several weeks or longer. The percutaneous catheter, comprising a long, flexible tube, is inserted into a large vein through an incision in the abdominal wall, chest wall, or upper extremity and threaded along the vein until the distal end reaches the heart. Central lines are also used for out-patient procedures such as long-term drug therapy and for hemodialysis, in which case the intention is that the catheter will remain in place for long time periods or permanently. An indwelling peritoneal catheter is used for drainage of abscises in advanced malignancy or liver disease, or to drain an abdominal abscess.

There are many diseases and medical conditions that require such percutaneous devices (such devices hereinafter also known as implants or percutaneous implants). For instance, patients with renal failure commonly require hemodialysis, which requires regular high-flow blood transfer that is presently provided through the surgical creation of an arteriovenus (AV) fistula. Unfortunately there are often problems maintaining continual access in these patients, and AV fistulas take time to mature before they can be used and often fail. In the interim, a chronic percutaneous catheter can be used to provide both arterial and venous access. However, long-term use of these percutaneous devices frequently results in infection. A device that permits long-term, infection-free access for the provision of hemodialysis would be extraordinarily useful to many patients who suffer renal failure.

Percutaneous mechanical cardiac assist devices include the intra-aortic balloon pump (IABP) and percutaneous ventricular assist devices (pVADs). The IABP comprises a catheter with an inflatable balloon at the distal end. The catheter is inserted into the femoral artery until the balloon is positioned in the descending thoracic aorta. The balloon can be inflated (in order to increase cardiac and systemic blood flow) and deflated (to decrease cardiac output, ventricular wall tension, and myocardial oxygen demand) in synchrony with the cardiac cycle, as required. pVADs are pumps that are surgically inserted into the ventricles of the heart to improve heart function in heart failure, to treat cardiogenic shock (for example, after cardiac arrest) or to maintain heart function while the patient is waiting for a heart transplant. pVADs may be inserted into the left ventricle (LVAD devices), right ventricle (RVAD) or into both ventricles (BiVAD). A percutaneous drive line is necessary to provide electrical power to operate the pump of either an IABP or a pVAD. Such devices may remain in place for weeks or months until either the heart regains full function or a transplant is performed or, increasingly, are intended to remain in place for the life of the patient.

Yet another example of a percutaneous device is a nephrostomy tube, a percutaneous catheter that is passed through the body wall and renal parenchyma and terminates in the renal pelvis, where urine collects prior to entering the ureter. The catheter is used to allow urinary drainage when the ureter or bladder is obstructed by injury or malignancy, or is not under voluntary control, for example, after a spinal cord injury. The nephrostomy tube can also be used to deliver drugs, such as chemotherapeutic agents, to the renal pelvis. Future medical devices such as a wearable artificial kidney, lung, or liver will require placement of permanent percutaneous lines to allow exchange of blood and/or gases between the body and the artificial organ.

The use of percutaneous implants extends into the prosthetic field. The direct attachment of a prosthetic limb to the residual bone of a patient's amputated limb provides many advantages over traditional socket attachment, including increased comfort of and utility to the patient. In a direct prosthetic attachment, a distal portion of residual bone of the patient's remaining limb (known as the "abutment") protrudes through the skin to allow attachment of the prosthetic device. A metal rod is inserted into the abutment. Such direct skeletal attachment provides a rigid connection of the prosthesis to the body and eliminates the need for a socket—a device which is worn over the residual limb or torso to permit attachment and suspension of the prosthesis, and use of which can cause pain, discomfort, or infection to an amputee. Direct attachment of the prosthesis to the residual bone also allows for better control of the prosthesis in space and more natural loading of the skeletal system. It provides an increased range of motion and improved mobility, allows increased activity levels, and, in the case of lower limb amputation, improves gait. An additional advantage is the provision of osseoperception, a sensation arising from mechanical stimulation by the bone-anchored prosthesis, which is transduced by mechanoreceptors in the muscle, joint, or surrounding tissues (Klineberg et al. 2005) such that the user perceives sensations of vibration from the prosthetic device.

A major impediment to the use of percutaneous medical devices like the ones described above is that a chronic open wound is created where the device passes through the skin. Infection of the exit wound created by the device is a frequent occurrence. Infection is an important consideration in any long- or short-term percutaneous implant. Infection may include superficial skin infections, deep tissue infection, or infection of bone (osteomyelitis). Bloodstream infections are a major cause of hospitalization and death in hemodialysis patients and significantly increase the cost of treatment. Cardiac assistive devices have very high rates of infection that endanger the patients who use them. Despite the potential benefits for prosthesis users, high infection rates have impaired the FDA approval of methods for direct skeletal attachment of prostheses. In sum, an infection in a wound surrounding a percutaneous device reduces quality of life and threatens a patient's health, and its treatment increases health care costs and may necessitate removal of the percutaneous device.

The inability to create a stable, permanent seal between the percutaneous implant and the surrounding skin causes a chronic exit wound that allows infection to develop. Two major factors contribute to the disruption of the skin-implant interface. The first factor involves different stiffness measurements between the implant and the surrounding skin. Human soft tissue, such as skin, has a low stiffness and a corresponding high compliance. When intact skin is pulled or stretched, its natural low stiffness/high compliance characteristics disperse the resulting forces over a large area of skin and subcutaneous tissue. Percutaneous implants, on the other hand, are made from material such as plastic or titanium that is more stiff/less compliant than human soft tissue. A rigid implant (such as one made from hard plastic or titanium) or a semi-rigid implant (such as one made from softer plastic material, such as that used in plastic tubing) allows relative motion between the implant and the surrounding soft tissue. When a rigid or semi-rigid percutaneous implant is in place, any pulling or stretching force applied to the implant is concentrated at the skin edge that surrounds the implant. The mechanical forces that pull on the skin lead to differential motion between the skin and the implant. This results in regression of the edge of the skin surrounding the implant, leading to a larger wound around the implant. Relative motion between the implant and surrounding soft tissues can also lead to fluid accumulation, which predisposes the skin-implant interface to infection. The second factor contributing to the disruption of the skin-implant interface is the apparent down growth of epithelial tissue into the wound, also known as the "marsupialization" of skin. Marsupialization can cause a pocket, or sulcus, to form around the implant, which allows debris and moisture to accumulate, facilitating infection and destabilizing the implant.

Previous attempts to prevent infection in the open wound surrounding a percutaneous device have included various strategies. Biological strategies include protein-coated devices, drug-releasing devices, and use of antimicrobial or antiseptic agents and dressings. Engineering strategies include new implant materials, new implant surface topographies, new implant structures or shapes, and addition of a stabilizing flange or cuff at or below the skin surface. For example, titanium implants with porous surfaces, or implants with hydroxyapatite coated subcutaneous flanges are known. Other subcutaneous systems, including implant umbrellas, metal flange implants, and subdermal meshes, provide greater surface area, which that increases the chances of infection of the implant. The goal of these subcutaneous implant approaches is to allow subdermal tissues to scar down on or into the implant, thus buffering the implant site against skin-stretching forces. For percutaneous prosthesis attachment, surgical strategies include attempts to attach skin directly to the bone. Some previous approaches have resulted in decreased infection rates in animal models, but all are still plagued by prohibitively high rates of skin marsupialization and infection. High infection rates have been seen in human trials.

Figure 8:
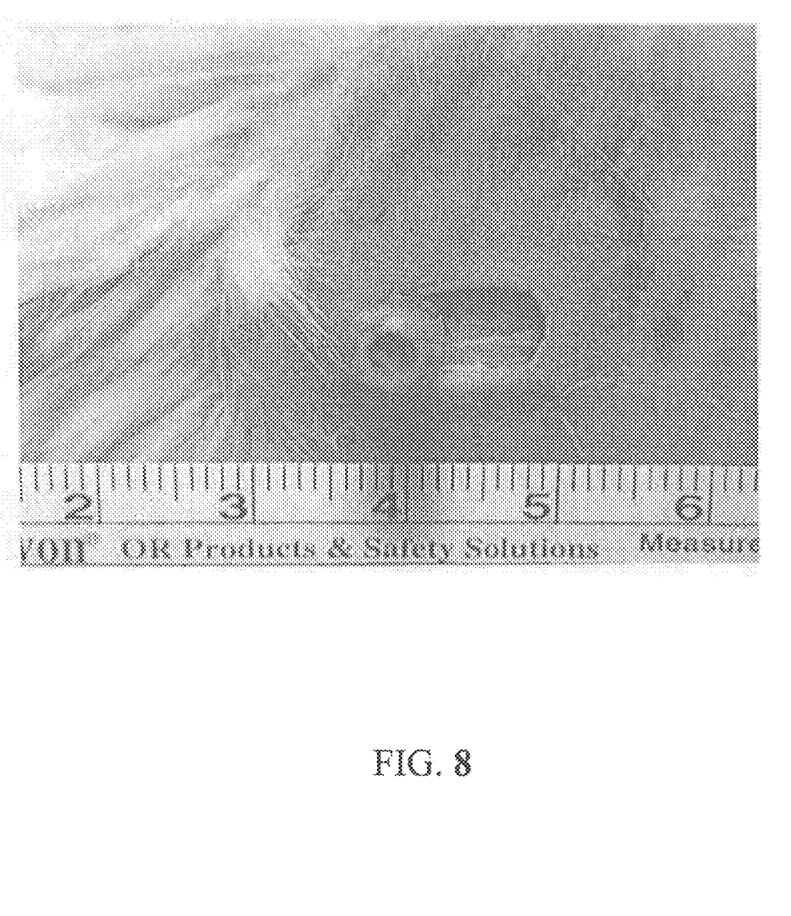
FIG. 8 shows skin erosion and increased wound size due to pressures caused by high stress forces acting at the skin-implant interface in the prior art; and Corresponding reference characters indicate corresponding elements among the view of the drawings. The headings used in the figures should not be interpreted to limit the scope of the claims.

Prior attempts to resolve compliance differences between skin and implant do not address the limitations overcome by the present invention. When a stiff material, such as a metal rod, sticks through the skin, a key issue is that forces are concentrated at that stiff material. The skin is pliable and would naturally stretch when pulled. However, the stiff rod prevents this stretching and the shear forces are all applied to the opposite side of the rod, just a few millimeters off the outer circumference. This causes high forces on the skin on that side of the rod. The skin erodes due to the pressures caused by these high shear forces and the wound gets larger as shown in FIG. 8. If the shear forces are always applied from one direction, the wound tends to elongate. If the shear forces are applied in many directions then the entire wound margin suffers and the wound increases in diameter globally. Furthermore, because they are not modular or because they are implanted directly into the skin, the prior art systems are difficult to remove and replace if a serious wound infection occurs or if the implant itself becomes infected.

Negative pressure has become a regularly applied therapy for many types of wounds. Negative pressure is sub-atmospheric pressure, and negative pressure therapy involves the application of sub-atmospheric pressure to a wound environment. Negative pressure therapy can facilitate wound healing through several primary mechanisms, including: (1) macrodeformation—drawing the wound edges together; (2) stabilization of the wound environment; (3) edema reduction and removal of wound exudates; and (4) microdeformation, which is stretch applied at the cellular level that stimulates cell growth. Secondary benefits attributed to negative pressure therapy include increased angiogenesis, enhanced formation of granulation tissue, and a reduction in the microbial bio-burden of the wound. Chronic application of negative pressure to a wound caused by a percutaneous device may prevent or limit the degree of marsupialization that occurs at the skin-implant interface. The prior art additionally fails to adequately address infection that is likely to develop in or around a percutaneous wound. Wound irrigation cannot be performed with conventional wound vacuum systems. The wound vacuum must be removed, the wound manually irrigated, and then the wound vacuum replaced.

SUMMARY

The present invention is directed towards an apparatus, herein known as a skin-implant interface device, for a percutaneous implant. According to aspects of the invention, the apparatus integrates the use of an external cap and a compliance gradient in order to improve the treatment and care of a patient. According to other aspects of the invention, the apparatus may further include the use of negative pressure to assist in the prevention of infection in or around the percutaneous wound. According to other aspects of the invention, the apparatus may also include a fluid treatment or air treatment system.

The foregoing and other aspects of the present invention will become apparent from the following detailed description of the invention when considered in conjunction with the accompanying drawings.

DETAILED DESCRIPTION

An embodiment of the present invention is directed to a stress shielding device that improves the treatment of a patient having a percutaneous implant. In one embodiment, the device includes an external cap and a compliance gradient, which together form a stress shield over the wound created by a percutaneous implant. The external cap and the compliance gradient are used to minimize or even prevent differential motion between the implant and surrounding soft tissues, a function referred to herein as "stress shielding." Stress shielding allows forces acting on the skin at the skin-implant interface to be dissipated over a larger surrounding area instead of being concentrated at the implant site. As forces upon the external cap and the compliance gradient are transferred to the skin, forces acting on the fixed percutaneous device are therefore transmitted to the skin over a greater surface area.

In one embodiment, the external cap is made of plastic, aluminum, metal, or other similar rigid or semi-rigid material. The cap is circular in shape, although other shapes may be employed instead. The rigid or semi-rigid nature of the central portion of the external cap is such that a sealed barrier may be formed around the implant. In one embodiment, the external cap is anchored to and surrounds the percutaneous device. Anchoring of the cap to the percutaneous implant may be accomplished using an O-ring seal, allowing for the cap to be easily attached and detached from the implant, or by other means well known in the art for attachment to implants.

The external cap is coupled to the top of the compliance gradient, using glue, pegs, or other coupling means. In one embodiment, the compliance gradient is arranged around the percutaneous implant site such that it surrounds, but does not cover, the implant wound. The compliance gradient is designed to dissipate said forces evenly and progressively away from the skin near the implant, thus minimizing force at any single skin location and providing a transition from the low stiffness (high compliance) of the surrounding skin to the higher stiffness (lower compliance) of the central cap and implant. As used herein, a "compliance gradient" is a flexible material whose stiffness decreases as the material extends away from its center. The outer edge of the compliance gradient has a high compliance and low stiffness, similar to that of skin. Together, the external cap and compliance gradient form a stress shield, with the cap serving as a rigid or semi-rigid structure, or the stiffest final element of the stress shield. The compliance of the stress shield progressively decreases, moving from the outer edge of the compliance gradient to the central portion of the external cap. The stress shield prevents shear forces from pulling on the skin adjacent to the percutaneous device, therefore protecting the skin around the implant from outside stresses.

There are several ways to provide the necessary radially-graded stiffness of the compliance gradient. In one embodiment, a flexible circular patch of material is adhered to the skin circumferentially around the percutaneous implant. This circular patch progressively increases in stiffness towards its center, with the outer area being only a little stiffer than the human skin and the patch stiffness gradually increasing toward the percutaneous implant. In this manner, shear forces caused by pulling on distant skin are distributed throughout the entire area under the patch and are therefore minimized at any one point on the skin. In another embodiment, a compliance gradient can be made that comprises multiple circular layers of a material, such as a skin dressing. The dressing may be circular in shape, but other shapes may also be used. In this embodiment, the initial layer of the dressing is adhered to the skin such that the dressing is centered about the implant. Each additional layer of dressing, with an area smaller than that of the previous layer, is adhered to the previous layer. Adding additional layers progressively increases the stiffness of the compliance gradient. As a result, the stiffness of the compliance gradient increases towards the implant in a graded fashion. In yet another embodiment, the compliance gradient is comprised of a material with a stiffness that is greater than that of skin and that is very thin at the outer circumference and progressively gets thicker toward the center. For a material with a given compliance, the thicker it is, the stiffer it is, and therefore the stiffness of the compliance gradient will decrease towards the periphery of the material in a graded fashion. Yet another embodiment uses a layer of material of an even thickness, that is circular in shape and centered about the implant, and in which the inherent stiffness of the material increases towards the center of the material. Alternately, the external cap and the compliance gradient could be made of the same piece of a material, such as plastic, using well known manufacturing means, whereby the material is progressively thinner as it extends radially away from the implant. In such an embodiment, the cap and compliance gradient would be "coupled" within the same material.

The compliance gradient allows stress concentrations in the skin to be transferred throughout the entire surface and is anchored by the external cap and percutaneous implant. When the peri-implant soft tissues are pulled or stretched, stress will be distributed in a controlled manner along the stress-shielding cap contact area and through the total surface area of the compliance gradient, thus decreasing the magnitude of the stress experienced at any one point along the interface. This force is transferred to and/or countered by the external cap and percutaneous abutment. The skin-implant interface 116 is shielded from stress concentrations, reducing forces that otherwise would produce peri-implant regression of the wound edges. The modular design of the invention allows for the percutaneous implant and/or the external cap to be easily removed (and later replaced) if a serious wound infection does occur or if the implant itself becomes infected.

In one embodiment of the invention, when the cap is attached over the compliance gradient, an empty space is created over the wound. A negative pressure adapter may be coupled to the cap, allowing negative pressure to flow between the space under the cap and the outside environment. The negative pressure adapter may take different forms, such as an opening allowing for insertion of a tube, or a tube that runs from the wound space around the abutment to the area outside of the external cap. Alternately, the negative pressure adapter may consist of a tube that runs from the wound area around the abutment to the area outside the cap, where it may end in a nozzle shaped for insertion into an external tube. Other adapters may also be employed. In one embodiment, the negative pressure adapter may be coupled to an external tube attached to a source of negative pressure, such as a vacuum pump or other sources that are well known in the art. When negative pressure is applied to the tubing, it creates a relative vacuum under the external cap and around the wound. Negative pressure encourages tissue proliferation at the skin-implant interface, providing a dynamic force to offset skin marsupialization around the implant. It further facilitates removal of fluid and exudates and increases wound perfusion (Orgill et al. 2009), thereby maintaining a healthy environment for the tissue around the implant.

Wound irrigation can be achieved by using said negative pressure to pull any desired fluid agent or solution through the wound. In one embodiment, a fluid treatment adapter is coupled to the cap to allow fluid to flow from the wound area. The fluid treatment adapter may take the same form as the negative pressure adapter, or it may take another form well known in the art for the flow of fluids. Said solutions or agents may be used to irrigate the wound to maintain general hygiene, to reduce or eliminate microbial colonization or biofilm formation, or to treat specific infections. This process may be performed manually or may be automated, for instance by using a microprocessor to control precise, specific treatment regimes, using the methods described in Lucio Di Jasio, "Programming 32-bit Microcontrollers in C: Exploring the PIC32" (Newnes, 2008 ed.), incorporated herein by reference. A plurality of irrigation agents may be used simultaneously or consecutively in simple or complex treatment regimes.

Referring to the drawings, embodiments of the device are illustrated and indicated numerically in FIGS. 1-13. In one embodiment (disclosed in FIG. 1) the device comprises an external cap 110. The external cap 110 surrounds a percutaneous implant 112 and serves to stress-shield the skin-implant interface 116, muscle 102, and subcutaneous tissues 104, from mechanical stresses by stabilizing the skin 106 surrounding the interface. The percutaneous implant 112 is a metal rod attached to residual bone 100 for the purpose of attaching a prosthetic device. In this embodiment, negative pressure is applied through a filter 118 at the skin/implant interface 116 via a low-pressure vacuum pump (50-125 mmHg) and vacuum tubing 114, which connects in an airtight manner via a negative pressure adapter to the external cap 110. The vacuum tubing 114 attaches to the negative pressure adapter of external cap 110 in order to establish negative pressure at the skin-implant interface. Filter 118 consists of a material appropriate for the filtering of negative pressure, such as a layer of granular foam. Tube 114 is connected to a source of negative pressure. An arrow 115 denotes the direction of air flow under vacuum though the tube 114. In the embodiment shown in FIG. 1, the external cap 110 is coupled to the skin 106 via one or more layers of a deformable material, such as thin layers of polymers, for forming a compliance gradient 108 that progressively decreases the stiffness in a radial fashion away from the percutaneous implant 112. In this embodiment, the rigid or semi-rigid external cap includes a passage, through which tubing is passed in order to allow application of negative pressure therapy. The negative pressure is generated by a small, portable pump 132 that can be worn by the patient. In the case of a skeletally-attached prosthetic device, the pump may be affixed to the prosthesis or directly incorporated into its design. Negative pressure can be applied to the skin/implant interface 116 either continuously or in a cyclical or intermittent fashion.

Figure 1:
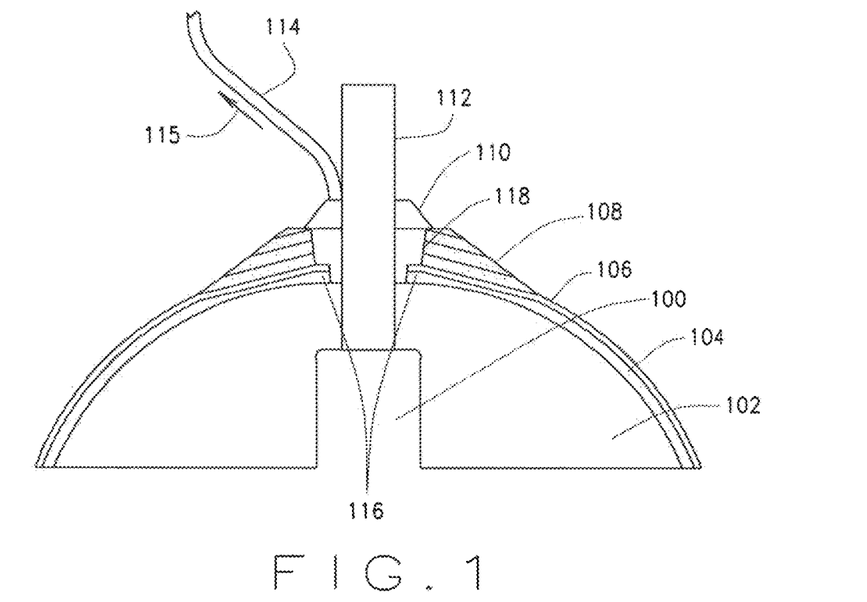
FIG. 1 is a diagram of an embodiment of the invention, showing the external cap attached to the percutaneous implant and in contact with the skin via a compliance gradient, which in this embodiment is made of a layered skin dressing.

In the embodiment shown in FIG. 1, a plurality of polymer layers are used to create the circular compliance gradient 108 between the uninvolved soft tissue (i.e. skin 106) and the external cap 110. The polymer layers of the compliance gradient 108 increase the stiffness and decrease the compliance of the surrounding skin 106 in two ways. First, because sheer forces are distributed along the circumference of the implant 112, a length determined by pi ($\pi$) multiplied by twice the radius, using a dressing layer of a larger diameter than the percutaneous wound area redistributes stress forces over a larger surface. For example, using a compliance gradient 108 with a 3 cm radius would distribute forces at its outer edge over a 6-fold larger area of skin compared to the force distribution upon the skin applied by a percutaneous rod with a 0.5 cm radius. Second, using a concentric compliance gradient 108 comprised of layers of material with decreasing radial size will progressively increase the stiffness closer to the central implant, thereby allowing the stress to be distributed across the entire circular surface area of the compliance gradient 108, while minimizing the compliance mismatch that occurs at any given interface. Overall, the combination of the stress shielding imparted by the external cap 110 and the surrounding compliance gradient 108 significantly reduces, or even eliminates, any stress at the skin-implant interface 116.

Figure 2:
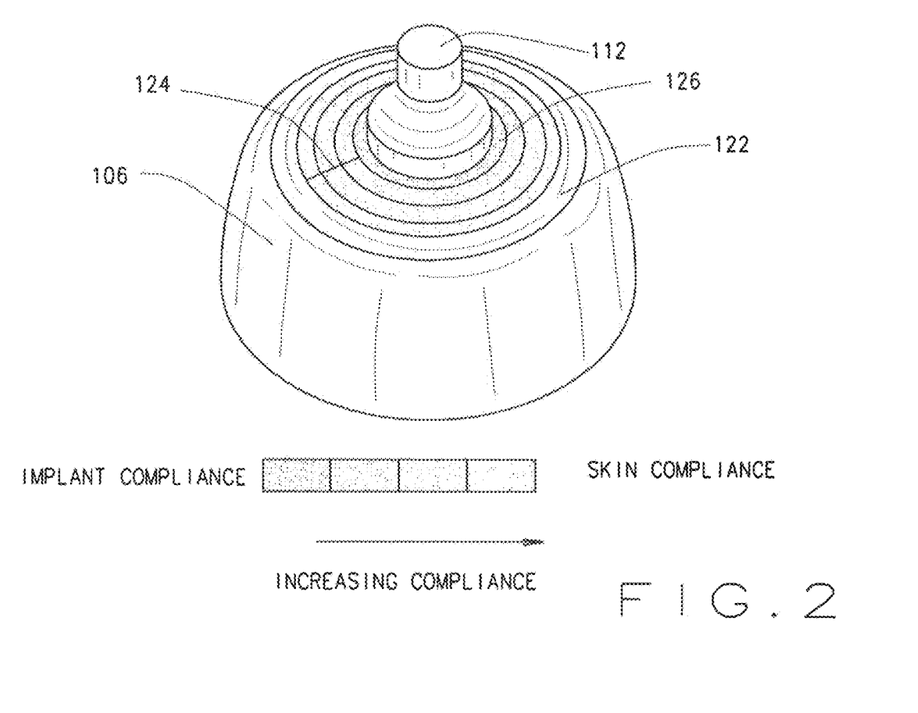
FIG. 2 is a three-dimensional view of the embodiment of FIG. 1 showing the layered skin dressing forming a radial compliance gradient between the implant and the surrounding skin.

Referring to FIG. 2, one embodiment of the compliance gradient 108 is disclosed in greater detail. In this embodiment, the compliance gradient 108 (shown in FIG. 1) may start with a 6 cm diameter dressing forming compliant base layer 122, which has approximately the same stiffness as skin (for example, DuoDERM®). Additional layers 124 and 126 of a stiffer dressing (for example, Tegaderm™, which is approximately 20 times stiffer than skin) with progressively smaller radii are layered concentrically on top and surrounding the implant providing a compliance gradient between the skin 106 and the implant 112. For example, 5 layers of Tegaderm™ would progressively increase stiffness to approximately 100 times the stiffness of skin, thus providing a gradual transition to the rigid or semi-rigid cap 110 shown in FIG. 1. It should be understood that any suitable number of layers can be added to achieve the necessary gradient in compliance between the implant and the surrounding skin.

Figure 3:
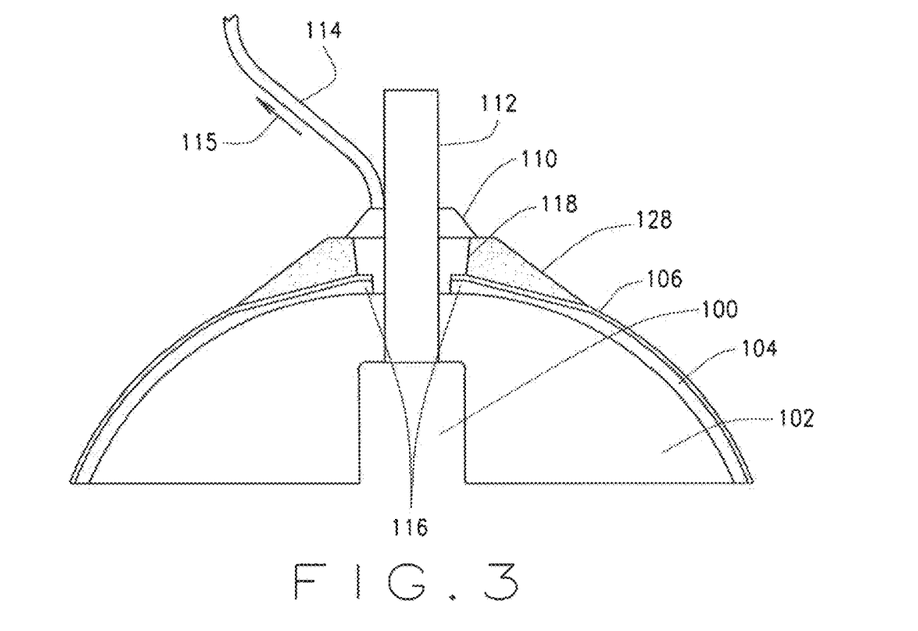
FIG. 3 is another alternative embodiment of the device in FIG. 1 showing a compliance gradient beneath the external cap.
Figure 4:
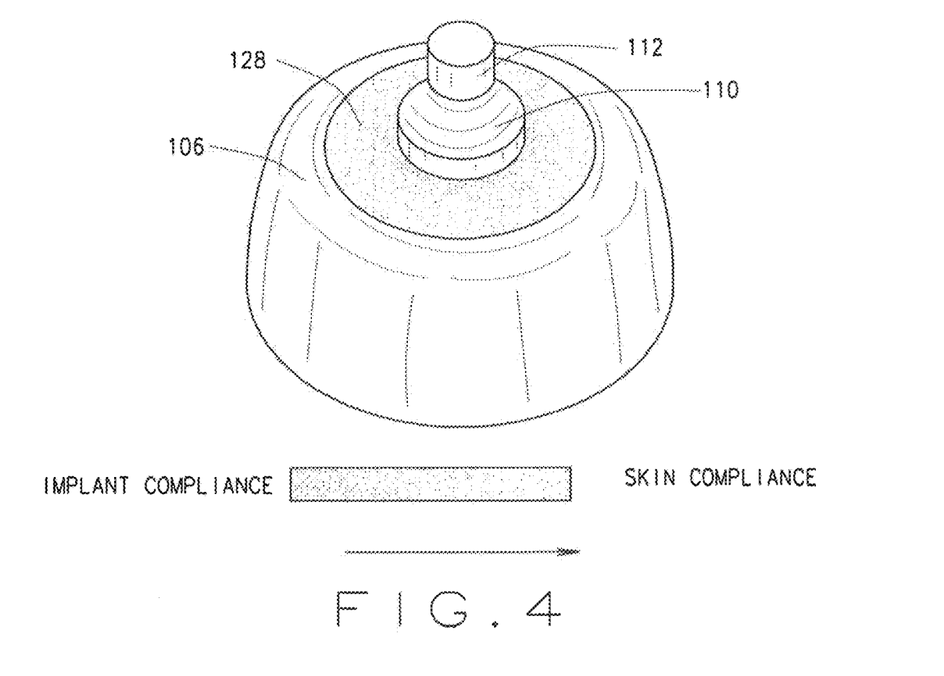
FIG. 4 is a three-dimensional view of the device in FIG. 3 showing a compliance gradient beneath the external cap.

Referring to FIGS. 3 and 4, another embodiment may incorporate a compliance gradient made of a single tapered layer of deformable material 128, such that the thin outer edge is very compliant and the compliance decreases progressively toward the center with increasing thickness of the material, the tapered material being placed under the rigid or semi-rigid cap 110 (FIG. 3). FIG. 4 shows another view of this embodiment. The radially-decreasing stiffness and increasing surface area of the compliance gradient 128 extending outwards from the external cap 110 will similarly enable the cap 110 to bridge the compliance mismatch between the percutaneous implant 112 and the surrounding skin 106.

Figure 5:
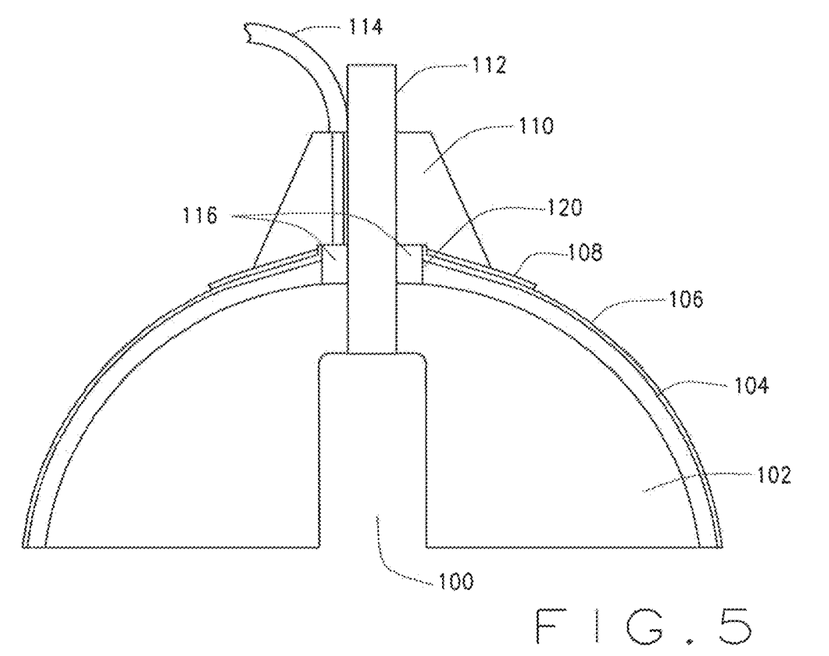
FIG. 5 is an alternative embodiment of the device in FIG. 1 showing a screen at the skin-implant interface instead of granulated foam.

Referring to FIG. 5, in an alternative embodiment negative pressure can also be applied through a screen 120 rather than through the granular foam 118 (FIG. 1). This may facilitate formation of a permanent seal through integration of the soft tissue with the implant screen 120, although the screen 120 could readily be replaced as desired.

Figure 6:
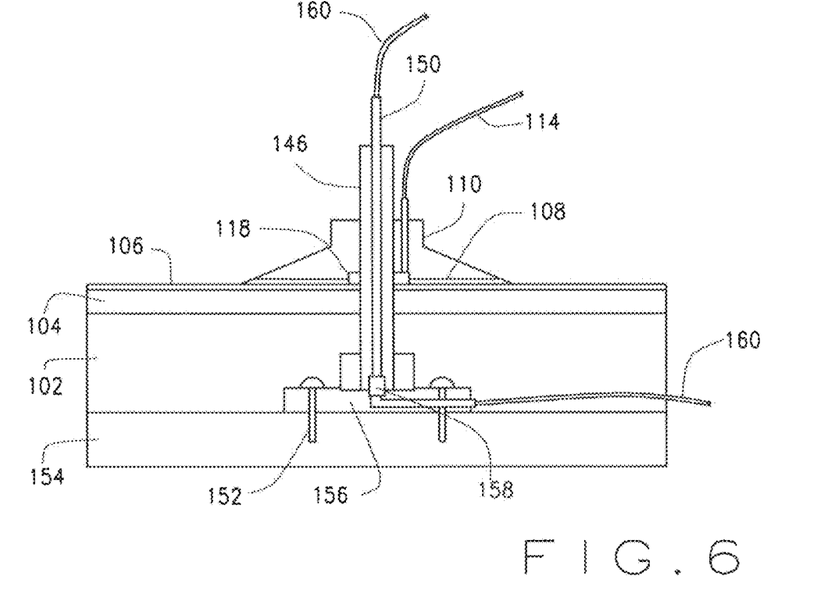
FIG. 6 shows an alternative embodiment of FIG. 1 wherein a percutaneous implant is mounted to a subcutaneous bone.

In another embodiment, shown in FIG. 6, a bone mount 156 would be surgically mounted to the surface of a suitable bone, such as a rib, the lower sternum, the long bone of the hip, or other suitable bone 154 using bone screws 152 or other suitable attachment devices. A hollow tube 146, which may be made of metal or other suitable material, would be attached to the bone mount. Wires, fluid lines, or other outlets 160 would be run for delivery and/or removal of ingests such as drugs, fluids, nutrition, blood products, gases, or power in order to treat conditions such as those described above. Outlets 160 provide venous access, arterial access, or access to any other internal organ system. Outlets 160 would be run through an external conduit 150 through hollow tube 146 and attach to the bone mount 156. The hollow tube 146 would be attached to the bone mount 156 by a coupler 158, which additionally seals together the internal ends of the hollow tube and the one or more outlets 160. Coupler 158 may include an O-ring seal or other tight elastic fitting known in the art, which may be opened and closed to start and stop fluid flow between the hollow tube 146 and outlets 160 and further allows the hollow tube to be disconnected from the bone mount 156 and removed. A compliance gradient 108 and external cap 110 surround the hollow tube 146. In addition, negative pressure therapy may be applied through vacuum line 114 as described herein and in accordance with one or more embodiments of the invention.

External application of a rigid or semi-rigid cap enables the residual bone (as in FIG. 1) or bone mount (as in FIG. 6) to be covered with well-vascularized muscle and other soft tissues. This is in contrast to methods used in some direct skeletal prosthesis attachment systems that require the overlying skin to be scarred to the bone around the percutaneous implant, resulting in relatively ischemic scar tissue around the implant. By allowing an interposed layer of well-vascularized muscle between the external cap and the bone mount, the oxygen tension within the peri-implant soft tissues is dramatically increased, as is the distance between the soft tissue-implant interface and underlying bone. Maintaining a robust and healthy tissue barrier drastically reduces the incidence of implant-associated infections, including osteomyelitis.

Figure 7:
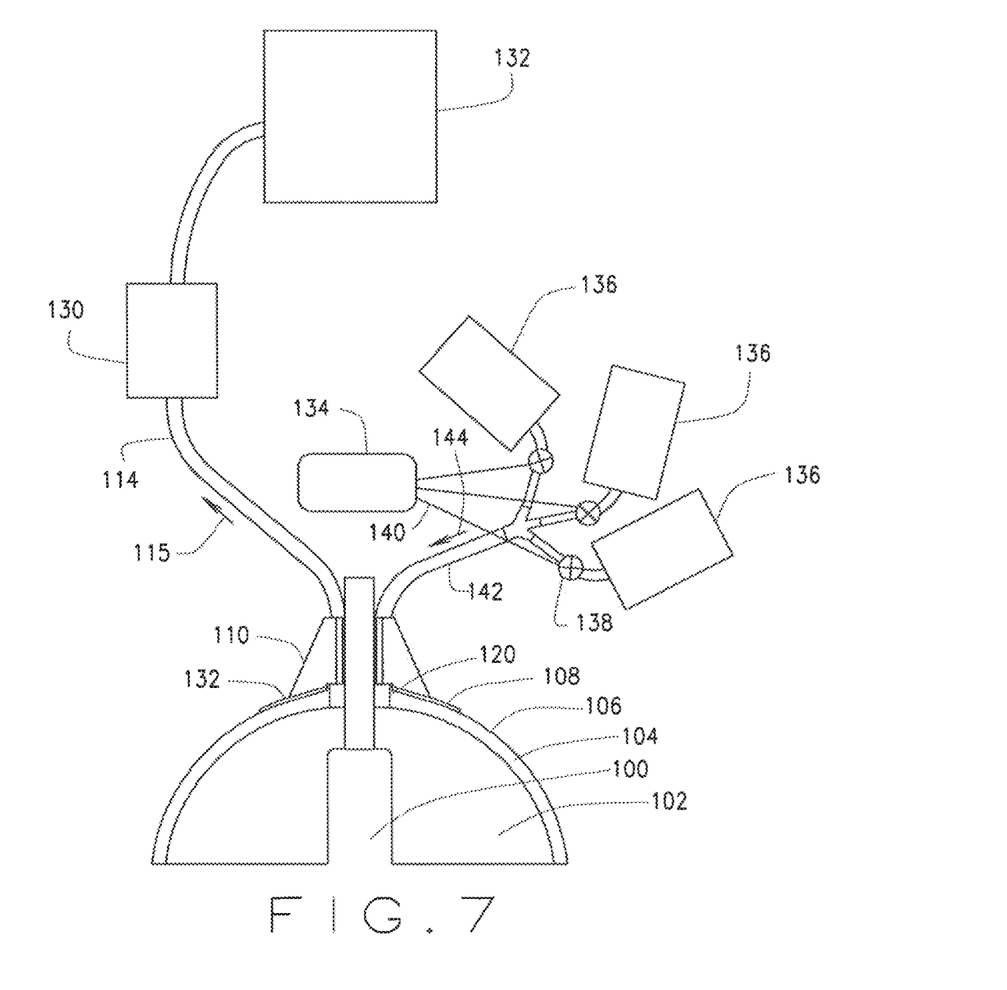
FIG. 7 shows a method for irrigating the skin-implant interface.

Another embodiment of the invention can be used in coordination with a fluid treatment system as an additional therapeutic option. The percutaneous opening created by a skin-implant interface is effectively a chronic wound that requires care in treatment. In this embodiment (FIG. 7), a fluid treatment system passes fluid treatments into and through the skin-implant interface 116. Referring to FIG. 7, this embodiment utilizes a fluid treatment adapter, tube 142, to deliver fluids from a fluid treatment system. Fluid treatment systems are known in the art, and may comprise a one or more electronic or manual valves 138 and one or more fluid reservoirs 136. The external cap 110 and compliance gradient 108 provide a stiffness that allows for the insertion of tube 142 and the corresponding flow of fluids to the patient's body. The desired fluid is pulled, under vacuum, from a reservoir 136 into and through the wound as desired. The arrow 144 indicates direction of fluid flow into the wound. A filter 130 can also placed on negative pressure line 114, if needed. Filter 130 traps particulate matter from wound exudates and used treatment fluids, preventing them from entering the pump 132. Other fluid treatment adapters could be employed, including a hole in the cap to allow for passage of tubing, or tubing that ends in a nozzle for connection to an external fluid treatment system. Removal of exudates or debris is facilitated using a fluid treatment system, keeping the wound clean.

In one embodiment, the precise amount of fluid to be delivered, the time of delivery, and the duration of delivery are readily determined using microprocessor 134 to control the pump and electronic valves 138 (FIG. 6) through electronic leads 140. In an alternative embodiment the said fluid delivery may be through manually controlled valves without use of the microprocessor 134.

In other embodiments, maintenance of venous access, arterial access, or access to any other internal organ system would be possible by use of the invention in combination with the appropriate implant. For example, two skin-implant interface devices of the kind described herein could be used for renal dialysis; one device would provide venous access and the other device would provide arterial access.

In another embodiment, one or more sensors can be used to monitor temperature, humidity (wetness), pH, ion concentrations, wound-exudate products or other relevant parameters at or around the wound location. Such sensors may be placed at the skin-abutment interface or at other suitable locations. Data from the sensors can be used by a microprocessor system to monitor the wound, or to control the vacuum or the delivery of desired fluids.

The use of a rigid or semi-rigid external cap combined with a compliance gradient allows easy use of various fluids or solutions to irrigate the wound, including normal saline, bacteriostatic agents, or tissue-sparing antiseptic agents, which may be used to minimize microbial colonization (biofilm) of the wound. Antibiotics or antifungal agents could also be used, as could fluids, including angiogenesis factors to enhance local blood supply to peri-implant tissues; bacteriophages to kill bacteria and minimize the biofilm; growth factors to enhance tissue growth at the skin-implant interface; or other suitable treatments. Alternately, tubing 142 (FIG. 7) could be connected to filtered air instead of a fluid treatment system, such that the vacuum could pull clean air through the wound if desired to dry the wound or alternatively to maintain a desired humidity.

Various different and apparent tube system designs are possible; for example in one embodiment, shown in FIG. 7, the fluid inlet tube 142 could be placed opposite from the primary vacuum tube 114. It also may be placed concentrically. Alternatively, more than one fluid treatment adapter may be used to provide the desired fluid flow.

From the preceding description, a number of advantages of one or more aspects, in various embodiments, of the invention are evident. It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An apparatus comprising:
an external cap surrounding a percutaneous implant;
a negative pressure adapter in fluid flow communication with a source of negative pressure for applying a negative pressure proximate the percutaneous implant; and
a compliance gradient positioned adjacent to the external cap, the compliance gradient defining a center aperture that surrounds the percutaneous implant and a peripheral edge that forms a periphery of the compliance gradient, wherein stiffness of the compliance gradient along the center aperture is greater than stiffness of the compliance gradient along the peripheral edge, wherein the compliance gradient comprises a plurality of concentric layers, wherein each layer of the plurality of concentric layers is a distinct layer, wherein the plurality of concentric layers have a variable stiffness that gradually decreases from the center aperture to the peripheral edge of the compliance gradient.

2. The apparatus of claim 1, wherein each of the plurality of concentric layers is a polymer layer.

3. The apparatus of claim 1, wherein each of the plurality of concentric layers has a radial size that progressively increases from a top layer to a bottom layer of the plurality of concentric layers.

4. The apparatus of claim 1, further comprising:
a filter in fluid flow communication with the source of negative pressure.

5. The apparatus of claim 4, wherein the filter comprises at least one of a screen or granular foam.

6. The apparatus of claim 1, further comprising:
a fluid treatment system comprising a source of fluid in selective fluid flow communication with at least one fluid treatment adapter, the at least one fluid treatment adapter being coupled to the external cap or the compliance gradient for providing the fluid proximate to the percutaneous implant.

7. The apparatus of claim 6, further comprising:
the fluid treatment system comprising at least one valve for controlling selective fluid flow communication from the source of fluid.

8. The apparatus of claim 7, further comprising: a microprocessor in operative communication with the at least one valve for controlling operation of the at least one valve between an open position that allows fluid flow communication and a closed position that prevents fluid flow communication.

9. The apparatus of claim 6, wherein the source of fluid in the fluid treatment system comprises at least one of a saline solution, a bacteriostatic agent, an antiseptic agent, and an antifungal agent.

10. The apparatus of claim 1, wherein thickness of the compliance gradient progressively increases from the peripheral edge to the center aperture of the compliance gradient.

11. The apparatus of claim 1, wherein a variable stiffness of the compliance gradient allows distribution of stress forces applied to the percutaneous implant to be redistributed along the peripheral edge of the compliance gradient.

12. The apparatus of claim 1, wherein the percutaneous implant comprises a hollow tubing.

13. The apparatus of claim 12, further comprising:
the negative pressure adapter being provided proximate a bone mount for attaching the percutaneous implant to bone tissue.

14. The apparatus of claim 12, further comprising an external conduit that is surrounded by the hollow tubing.

15. The apparatus of claim 14, further comprising:
one or more outlets configured to be disposed within the external conduit.

16. The apparatus of claim 1, wherein the percutaneous implant comprises a catheter.

17. The apparatus of claim 1, wherein the percutaneous implant comprises a prosthetic limb.

18. An apparatus comprising:
an external cap configured to surround a percutaneous implant;
a negative pressure adapter in fluid flow communication with a source of negative pressure for applying a negative pressure proximate the percutaneous implant; and
a compliance gradient positioned adjacent to the external cap, the compliance gradient defining a center aperture that is configured to surround the percutaneous implant and a peripheral edge that forms a periphery of the compliance gradient, wherein stiffness of the compliance gradient along the center aperture is greater than stiffness of the compliant gradient along the peripheral edge, wherein the compliance gradient is not configured to penetrate skin that surrounds the percutaneous implant.

19. The apparatus of claim 18, wherein the compliance gradient is configured to adhere to skin that surrounds the percutaneous implant.

20. The apparatus of claim 18, wherein the compliance gradient comprises a plurality of distinct layers.

21. The apparatus of claim 20, wherein each of the plurality of distinct layers is a polymer layer.

22. The apparatus of claim 20, wherein each of the plurality of distinct layers has a radial size that progressively increases from a top layer to a bottom layer of the plurality of distinct layers.

23. The apparatus of claim 18, further comprising:
a filter in fluid flow communication with the source of negative pressure.

24. The apparatus of claim 23, wherein the filter comprises at least one of a screen or granular foam.

25. The apparatus of claim 18, further comprising:
a fluid treatment system comprising a source of fluid in selective fluid flow communication with at least one fluid treatment adapter, the at least one fluid treatment adapter being coupled to the external cap or the compliance gradient for providing the fluid proximate to the percutaneous implant.

26. The apparatus of claim 25, further comprising:
the fluid treatment system comprising at least one valve for controlling selective fluid flow communication from the source of fluid.

27. The apparatus of claim 26, further comprising:
a microprocessor in operative communication with the at least one valve for controlling operation of the at least one valve between an open position that allows fluid flow communication and a closed position that prevents fluid flow communication.

28. The apparatus of claim 25, wherein the source of fluid in the fluid treatment system comprises at least one of a saline solution, a bacteriostatic agent, an antiseptic agent, and an antifungal agent.

29. The apparatus of claim 18, wherein thickness of the compliance gradient progressively increases from the peripheral edge to the center aperture of the compliance gradient.

30. The apparatus of claim 18, wherein a variable stiffness of the compliance gradient allows distribution of stress forces applied to the percutaneous implant to be redistributed along the peripheral edge of the compliance gradient.

31. The apparatus of claim 18, wherein the percutaneous implant comprises a hollow tubing.

32. The apparatus of claim 31, further comprising:
   the negative pressure adapter being provided proximate a bone mount for attaching the percutaneous implant to bone tissue.

33. The apparatus of claim 31, further comprising an external conduit that is surrounded by the hollow tubing.

34. The apparatus of claim 33, further comprising:
   one or more outlets configured to be disposed within the external conduit.

35. The apparatus of claim 18, wherein the percutaneous implant comprises a catheter.

36. The apparatus of claim 18, wherein the percutaneous implant comprises a prosthetic limb.

\* \* \* \* \*